United States Patent
Matsumura et al.

(10) Patent No.: US 8,797,177 B2
(45) Date of Patent: Aug. 5, 2014

(54) MEDICAL TELEMETRY SYSTEM AND MEDICAL TELEMETER

(75) Inventors: Fumiyuki Matsumura, Tokyo (JP); Hirokazu Hatakeyama, Tokyo (JP); Hiroyuki Taniguchi, Tokyo (JP); Shinji Tezuka, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 447 days.

(21) Appl. No.: 13/237,411

(22) Filed: Sep. 20, 2011

(65) Prior Publication Data

US 2012/0068855 A1 Mar. 22, 2012

(30) Foreign Application Priority Data

Sep. 21, 2010 (JP) ................................ 2010-210802
Jun. 1, 2011 (JP) ................................ 2011-123437

(51) Int. Cl.
G08B 23/00 (2006.01)

(52) U.S. Cl.
USPC ............. 340/870.02; 340/539.1; 340/539.11; 340/539.12; 340/539.13; 340/573.1

(58) Field of Classification Search
USPC ................... 340/870, 539.1, 539.11, 539.12, 340/539.13, 573.1
See application file for complete search history.

(56) References Cited

U.S. PATENT DOCUMENTS

| | | | |
|---|---|---|---|
| 6,364,834 B1 * | 4/2002 | Reuss et al. .................. | 600/300 |
| 2005/0027197 A1 | 2/2005 | Segawa et al. | |
| 2005/0171444 A1 | 8/2005 | Ono et al. | |
| 2006/0202816 A1 * | 9/2006 | Crump et al. ............ | 340/539.12 |
| 2006/0226992 A1 * | 10/2006 | Al-Ali et al. ............... | 340/573.1 |
| 2008/0300470 A1 * | 12/2008 | Gerber et al. ................. | 600/301 |
| 2009/0112626 A1 * | 4/2009 | Talbot et al. ..................... | 705/3 |
| 2009/0118595 A1 * | 5/2009 | Greiner et al. ............... | 600/301 |
| 2009/0171169 A1 | 7/2009 | Nagata | |
| 2010/0160742 A1 | 6/2010 | Seidl et al. | |
| 2011/0196218 A1 | 8/2011 | Nomura et al. | |

FOREIGN PATENT DOCUMENTS

| | | |
|---|---|---|
| JP | 2005-000344 A | 1/2005 |
| JP | 2005-168600 A | 6/2005 |
| JP | 2009-136372 A | 6/2009 |
| JP | 2010-85258 A | 4/2010 |

OTHER PUBLICATIONS

Extended European Search Report, issued by the European Patent Office in corresponding European Application No. 11182057.7 on Dec. 29, 2011.
Communication from the Japanese Patent Office dated Mar. 28, 2014, in a counterpart Japanese application No. 2011-123437.

* cited by examiner

*Primary Examiner* — Daryl Pope
(74) *Attorney, Agent, or Firm* — Sughrue Mion, PLLC

(57) ABSTRACT

A medical telemetry system includes: a medical telemeter including: a measuring portion which measures a biological signal of a patient as biological signal data; a communicating portion which wirelessly transmits the biological signal data; and a connection information storing portion which stores connection information; and a receiver including: a non-contact communicating portion which executes first non-contact communication to read the connection information in a non-contact manner; a storage portion which stores the connection information read by the non-contact communicating portion; and a receiving portion which starts reception of the biological signal data transmitted by the communicating portion, when the connection information is stored in the storage portion.

21 Claims, 9 Drawing Sheets

MEDICAL TELEMETRY SYSTEM AND MEDICAL TELEMETER

BACKGROUND OF THE INVENTION

The present invention relates to a medical telemetry system including a telemeter (transmission apparatus) which wirelessly transmits biological signal data that are acquired by measuring the blood pressure, heart rate, and the like of a living body, and a receiver which remotely receives the biological signal data.

In an inpatient ward of a hospital or the like, such a medical telemetry system has been used for monitoring the condition of a patient. JP-A-2005-168600 discloses a related-art telemeter which is portable by a patient. A patient can freely move in an inpatient ward while measurements of biological signals are continued. A specific carrier frequency (wireless communication channel) which is used for wirelessly transmitting biological signal data to a receiver is allocated to the telemeter.

An example of such a receiver is a central monitor which is disposed in a nurse's station or the like. A receiver of this kind can receive biological signal data which are transmitted through a plurality of channels, and can receive biological signal data transmitted from a plurality of telemeters which are attached to different patients, to collectively display and record the data.

In order to adequately manage biological signal data transmitted from telemeters, information of a patient must be correctly corresponded to information for establishing communication (for example, the channel number and the production number of the apparatus). The work of establishing correspondence is manually performed on the side of a central monitor. For example, a case where a telemeter to which channel 1 is allocated is to be attached to patient A, and that to which channel 2 is allocated is to be attached to patient B will be considered. An operation of corresponding channel 1 to patient A and channel 2 to patient B is adequately performed on the side of the central monitor, and the correspondence relationships are stored in a storage portion of the central monitor. Thereafter, a reception channel is adequately selected, so that biological signal data which are acquired by measuring patients A and B can be displayed collectively or selectively. In the case where the manual input is not correctly carried out, such as that, while the telemeters are attached respectively to patients A and B as described above, the channel numbers are erroneously input so that channel 1 is corresponded to patient B and channel 2 is corresponded to patient A, biological signal data of patient A which is remotely monitored through channel 1 are recognized as those of patient B, and biological signal data of patient B which is remotely monitored through channel 2 are recognized as those of patient A. Misidentification of patients under remote monitoring may cause a serious medical accident.

By contrast, even in the case where the correspondence relationships between the patients and the channels are correctly input on the side of the central monitor, when the telemeters are not correctly attached to the patients, a similar situation occurs. In the case where an input operation is performed on the side of the central monitor so that channel 1 is corresponded to patient A and channel 2 is corresponded to patient B, when the telemeter to which channel 1 is allocated is attached to patient B, and that to which channel 2 is allocated is attached to patient A, for example, medical biological signal data of patient B are input to channel 1 which should receive those of patient A, and biological signal data of patient A are is input to channel 2 which should receive those of patient B. The related-art telemeter disclosed in JP-A-2005-168600 includes a display device which displays measured biological signal data, but does not have a function of displaying information which can identify a patient. Therefore, the possibility that a telemeter is attached to a patient who is different from the original one cannot be eliminated.

SUMMARY

It is therefore an object of the invention to provide a medical telemetry system in which information for establishing communication to enable a biological signal transmitted from a telemeter to be received by a receiver, and that identifying a patient are easily corresponded to each other, whereby a medical accident can be prevented from occurring, and also a medical telemeter which is to be used in the system.

In order to achieve the object, according to the invention, there is provided a medical telemetry system comprising: a medical telemeter including: a measuring portion which measures a biological signal of a patient as biological signal data; a communicating portion which wirelessly transmits the biological signal data; and a connection information storing portion which stores connection information; and a receiver including: a non-contact communicating portion which executes first non-contact communication to read the connection information in a non-contact manner; a storage portion which stores the connection information read by the non-contact communicating portion; and a receiving portion which starts reception of the biological signal data transmitted by the communicating portion, when the connection information is stored in the storage portion.

The receiver may further include a first patient information storing portion which stores patient information for identifying the patient, the medical telemeter may further include a second patient information storing portion. The non-contact communicating portion of the receiver may execute second non-contact communication to write the patient information that is stored in the first patient information storing portion in the second patient information storing portion in a non-contact manner, when the non-contact communicating portion executes the first non-contact communication.

The medical telemeter may further include a transmission-side displaying portion which displays the patient information stored in the second patient information storing portion.

The patient information may include at least one of character information and image information.

The receiver may further include a reception-side displaying portion which displays at least one of the biologic signal data and the patient information and the connection information in a manner that the patient information and the connection information correspond to each other.

The receiver may issue an alarm when a state where the patient information is not corresponded to the connection information in one-to-one relationship is detected.

The communicating portion of the medical telemeter may transmit patient information which is stored in the second patient information storing portion to the receiving portion of the receiver together with the biological signal data, and the receiver may compare the patient information that is received by the receiving portion with the patient information that is stored in the first patient information storing portion of the receiver, and the receiver may issue an alarm, when a state where the patient information that is received by the receiving portion and the patient information that is stored in the first patient information storing portion are different from each other is detected.

The connection information storing portion may include one of an RFID chip, a bar code, and a two-dimensional code.

The second patient information storing portion may include an RFID chip.

The connection information may include one of a wireless communication channel, a device identification number, an IP address, and a MAC address.

The medical telemeter may include a transmitter which is portable by the patient, and the receiver may include at least one of a bedside monitor and a central monitor.

The medical telemeter may include at least one of a transmitter which is portable by the patient, a bedside monitor, and a central monitor, and the receiver may include a portable information terminal.

When the non-contact communicating portion of the receiver executes the first non-contact communication, times which are internally managed in the medical telemeter and the receiver respectively may be synchronized with each other.

When the non-contact communicating portion of the receiver executes one of the first non-contact communication and the second non-contact communication, times which are internally managed in the medical telemeter and the receiver respectively may be synchronized with each other.

The medical telemetry system may further include a read/communication device which, from a patient information storing portion, which is to be attached to a patient and which stores patient information identifying the patient, reads the patient information, and which transmits the read patient information to the communicating portion of the medical telemeter.

The medical telemetry system may further include a read/communication device which, from a third patient information storing portion, which is to be attached to a patient and which stores patient information for identifying the patient, reads the patient information, the read/communication device which executes at least one of transmission of the patient information read from the third patient information storing portion to the communicating portion of the medical telemeter, and reception of the patient information stored in the second patient information storing portion of the medical telemeter from the communicating portion of the medical telemeter.

The communicating portion of the medical telemeter may transmit the patient information received from the read/communication device, to the receiver.

The read/communication device may execute the reception of the patient information from the communicating portion of the medical telemeter, and the read/communication device may issue an alarm when the patient information read from the third patient information storing portion is not coincident with the patient information received from the communicating portion of the medical telemeter.

The read/communication device may execute the transmission of the patient information to the communicating portion of the medical telemeter, and the medical telemeter may issue an alarm when the patient information received from the read/communication device is not coincident with the patient information stored in the second patient information storing portion.

The receiver may issue an alarm when the patient information received from the communicating portion of the medical telemeter is not coincident with the patient information stored in the second patient information storing portion.

In order to achieve the object, according to the invention, there is also provided a medical telemeter which is to be used in the medical telemetry system.

DETAILED DESCRIPTION OF EMBODIMENTS

Figure 1:
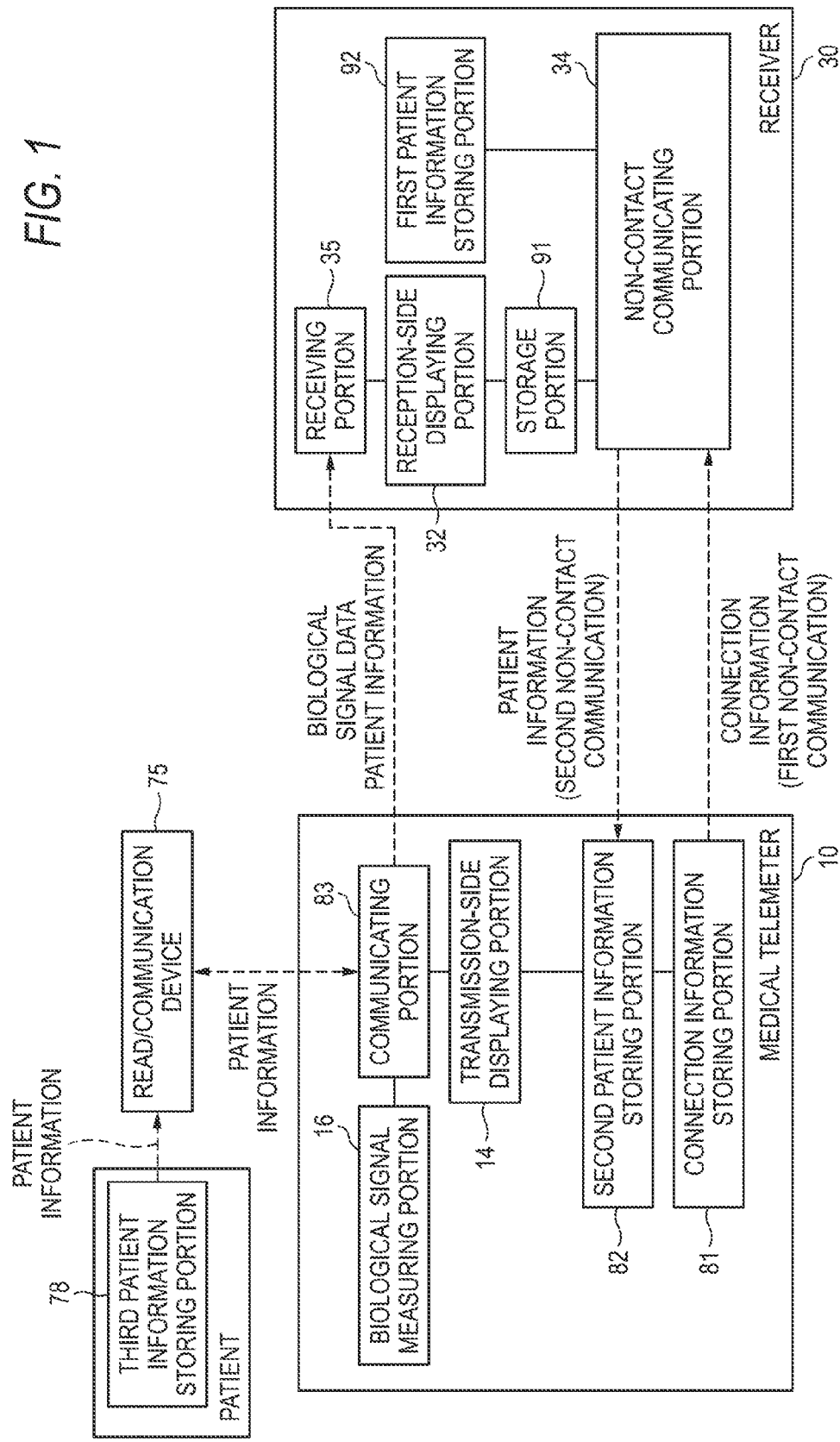
FIG. 1 is a block diagram schematically showing the concept of the invention.

Hereinafter, embodiments of the invention will be described with reference to the accompanying drawings. First, the concept of the invention will be described with reference to FIG. 1.

The medical telemetry system of the invention is configured by a medical telemeter 10 (hereinafter, referred to merely as the telemeter 10), and a receiver 30. The telemeter 10 includes a biological signal measuring portion 16 (measuring portion) which can measure biological signals of a patient as biological signal data, and a communicating portion 83 which can wirelessly transmit the biological signal data. The receiver 30 includes a receiving portion 35 which can receive the biological signal data transmitted from the communicating portion 83.

The telemeter further includes a connection information storing portion 81 which stores connection information (for example, the wireless communication channel, the device identification number, the IP address, and the MAC address) related to setting required for enabling the receiving portion 35 to receive the biological signal data transmitted from the communicating portion 83. Examples of the connection information storing portion 81 are an RFID chip, a bar code, and a two-dimensional code.

The receiver 30 includes: a non-contact communicating portion 34 that can execute first non-contact communication in which the connection information is read in a non-contact manner; and a storage portion 91 that stores the connection information read by the non-contact communicating portion 34. The receiving portion 35 is configured so that, when the connection information is stored in the storage portion 91, the reception of the biological signal data is started.

According to the configuration, the inputting operation is performed by means of non-contact communication, and therefore, matching (correspondence) of patient information and connection information is not required to be manually performed. Consequently, the configuration can contribute to laborsaving, and prevent a medical accident due to an erroneous input from occurring.

A configuration may be employed in which (1) the receiver 30 further includes a first patient information storing portion 92 that can store patient information identifying a patient, (2) the telemeter 10 further includes a second patient information storing portion 82 that can store the patient information, and (3), when the first non-contact communication is to be performed, the non-contact communicating portion 34 can execute second non-contact communication in which the patient information stored in the first patient information storing portion 92 is written in the second patient information storing portion 82 in a non-contact manner. In this case, preferably, the first non-contact communication and the second non-contact communication are of the same kind so that a medical person can execute by one operation the first non-contact communication and the second non-contact communication.

According to the configuration, transmission of patient information from the receiver 30 to the telemeter 10 can be performed in conjunction with that of connection information from the telemeter 10 to the receiver 30. Without requiring a manual inputting work which is cumbersome, and which may possibly cause an error, the telemeter 10 and the receiver 30 can be caused by one operation to share connection information and patient information.

The telemeter 10 may be configured so as to include a transmission-side displaying portion 14 which can display the patient information stored in the second patient information storing portion 82.

According to the configuration, patient information is displayed on the transmission-side displaying portion 14 disposed in the telemeter 10 which is directly attached to the patient, and hence a medical person can easily check the patient by viewing the transmission-side displaying portion 14. Therefore, an accident in which a medical person erroneously attaches a medical telemeter to a patient who is different from the original one can be prevented from occurring.

The receiver 30 may be configured so as to include a reception-side displaying portion 32 which can correspondingly display the patient information and the connection information. The receiver 30 may be configured so as to issue an alarm when a state where the patient information is not corresponded to the connection information in one-to-one relationship is detected.

A configuration may be employed in which (1) the communicating portion 83 can transmit patient information stored in the second patient information storing portion 82 to the receiving portion 35 together with the biological signal data, and (2) the receiver 30 compares the patient information received by the receiving portion 35 with the patient information which is stored in first patient information storing portion 92 correspondingly to the connection information identifying the telemeter 10 that transmits the biological signal data received by the receiving portion 35, and, if a state where they are different from each other is detected, issues an alarm.

According to these configurations, erroneous attachment which may be possible in a medical telemetry system including a plurality of telemeters, and in which a telemeter is attached to a patient who is different from the original one can be effectively prevented from occurring.

Examples of non-contact communication are RFID communication, code reading, and short-distance wireless communication such as infrared communication. Examples of the non-contact communicating portion 34 are an RFD reader/writer, bar code reader, and scanner which are used depending on the kind of non-contact communication, and may be externally or internally mounted on the receiver.

When the first non-contact communication or the second non-contact communication is executed, the times which are internally managed in the telemeter 10 and the receiver 30 respectively may be synchronized with each other.

According to the configuration, it is possible to prevent a situation where a temporal discrepancy is produced between the biological signal measured by the telemeter 10 and that received by the receiver 30, from occurring.

A configuration may be employed in which (1) the medical telemetry system further includes a read/communication device 75 which can read the patient information from a third patient information storing portion 78 that is to be attached to a patient, and that stores patient information identifying the patient, and (2) the read/communication device 75 can execute at least one of transmission of the patient information read from the third patient information storing portion 78 to the communicating portion 83 of the medical telemeter 10, and reception of the patient information stored in the second patient information storing portion 82 from the communicating portion 83 of the medical telemeter 10.

The communicating portion 83 of the medical telemeter 10 may be configured so as to be able to transmit the patient information received from the read/communication device 75, to the receiver 30.

According to these configurations, when the medical telemeter 10 is to be attached to a patient, the correspondence relationship between the patient and the medical telemeter can be rechecked, and therefore it is possible to more surely prevent a medical accident due to misidentification of patients, from occurring.

The read/communication device 75 may be configured so as to issue an alarm when the patient information read from the third patient information storing portion 78 is not coincident with that received from the communicating portion 83 of the medical telemeter 10.

The medical telemeter 10 may be configured so as to issue an alarm when the patient information received from the read/communication device 75 is not coincident with that stored in the second patient information storing portion 82.

The receiver 30 may be configured so as to issue an alarm when the patient information received from the communicating portion 83 of the medical telemeter 10 is not coincident with that stored in the first patient information storing portion 92.

According to these configurations, the correspondence relationship between the patient and the medical telemeter can be easily rechecked without imposing a burden of visual checking on a medical person.

Examples of the medical telemeter are a transmitter which is portable by a patient, a bedside monitor, and a central monitor. Examples of the receiver are a bedside monitor, a central monitor, and a portable information terminal.

Figure 2:
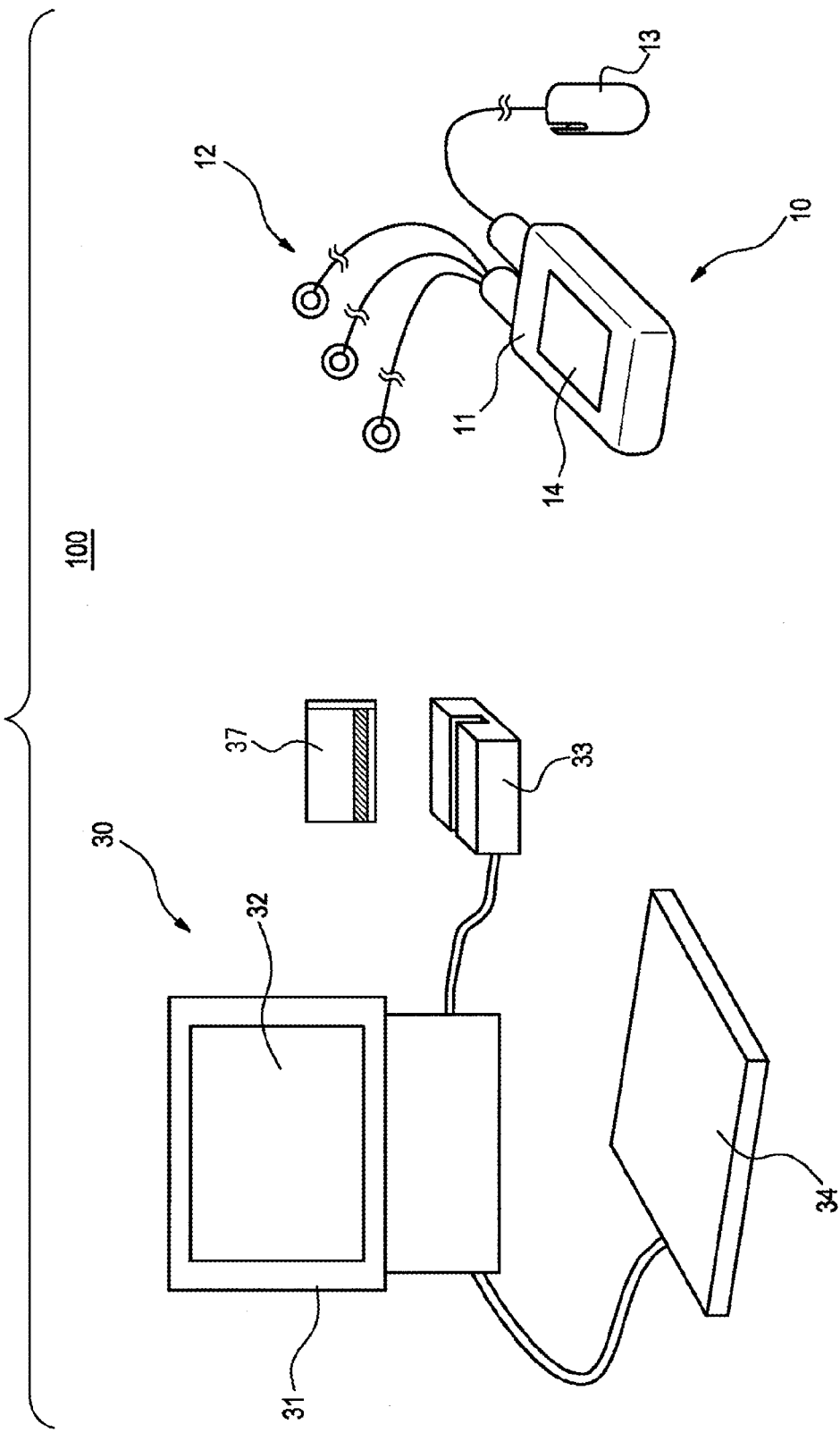
FIG. 2 is a view schematically showing a medical telemeter and receiver which constitute a medical telemetry system of a first embodiment of the invention.

Next, a medical telemetry system 100 of a first embodiment of the invention will be described with reference to FIG. 2.

The telemeter 10 includes the telemeter body unit 11, an electrode group 12, a sensor probe 13, and a transmission-side displaying portion 14. The telemeter body unit 11 is configured so as to have the size and weight which allow a patient to carry it or move together therewith.

The electrode group 12 is to be attached to the chest region or limbs of a patient to detect an electrocardiogram, aspiration, and the like of the patient, and electrically connected to the telemeter body unit 11 through an electrode lead wire group.

The sensor probe 13 is attached to a finger of a patient to detect the pulse wave and blood oxygen saturation (SpO2) of the patient, and electrically connected to the telemeter body unit 11 through a sensor lead wire. The telemeter body unit 11 is configured so as to be connectable to a cuff which is not shown, and therefore it is possible to measure the non-invasive blood pressure (NIBP). The biological signals which can be measured by the electrode group 12 and the sensor probe 13 are mere examples and not limited to the above-described ones.

The transmission-side displaying portion 14 is disposed in the telemeter body unit 11. The telemeter body unit 11 performs calculation processes on various biological signal data measured by the electrode group 12 and the sensor probe 13, and data which are visualized in the form of numbers or waveforms are displayed on the transmission-side displaying portion 14.

A transmitting portion which will be described later is disposed in the telemeter body unit 11, so that the measured various biological signal data can be wirelessly transmitted to the receiver 30.

The receiver 30 includes a body unit portion 31, the reception-side displaying portion 32, a patient information reading portion 33, and the non-contact communicating portion 34.

A receiving portion 35 which will be described later in detail is disposed in the body unit portion 31, so that the various biological signals which are wirelessly transmitted from the telemeter 10 can be received.

The reception-side displaying portion 32 is disposed in the body unit portion 31. The body unit portion 31 performs calculation processes on various biological signal data received by the receiving portion 35, and data which are visualized in the form of numbers or waveforms are displayed on the reception-side displaying portion 32.

The patient information reading portion 33 is a device which acquires patient information identifying a patient from an ID card 37 on which the patient information is stored, and communicably connected to the body unit portion 31 through a cable. For example, the patient information reading portion 33 may be configured as a card reader which reads patient information that is stored in the form of magnetic information on the ID card 37, or as a code reader which reads patient information that is stored in the form of a bar code or a two-dimensional code on the ID card 37. The patient information reading portion 33 may be wirelessly connected to the body unit portion 31 as far as the patient information reading portion is communicable to the body unit portion.

The non-contact communicating portion 34 is communicably connected to the body unit portion 31 through a cable. When the portion is communicable to the body unit portion 31, they are wirelessly connected to each other. The non-contact communicating portion 34 is configured so as to be communicable in a non-contact manner to an RFID tag circuit 20 (described later in detail) disposed in the telemeter body unit 11.

Figure 3:
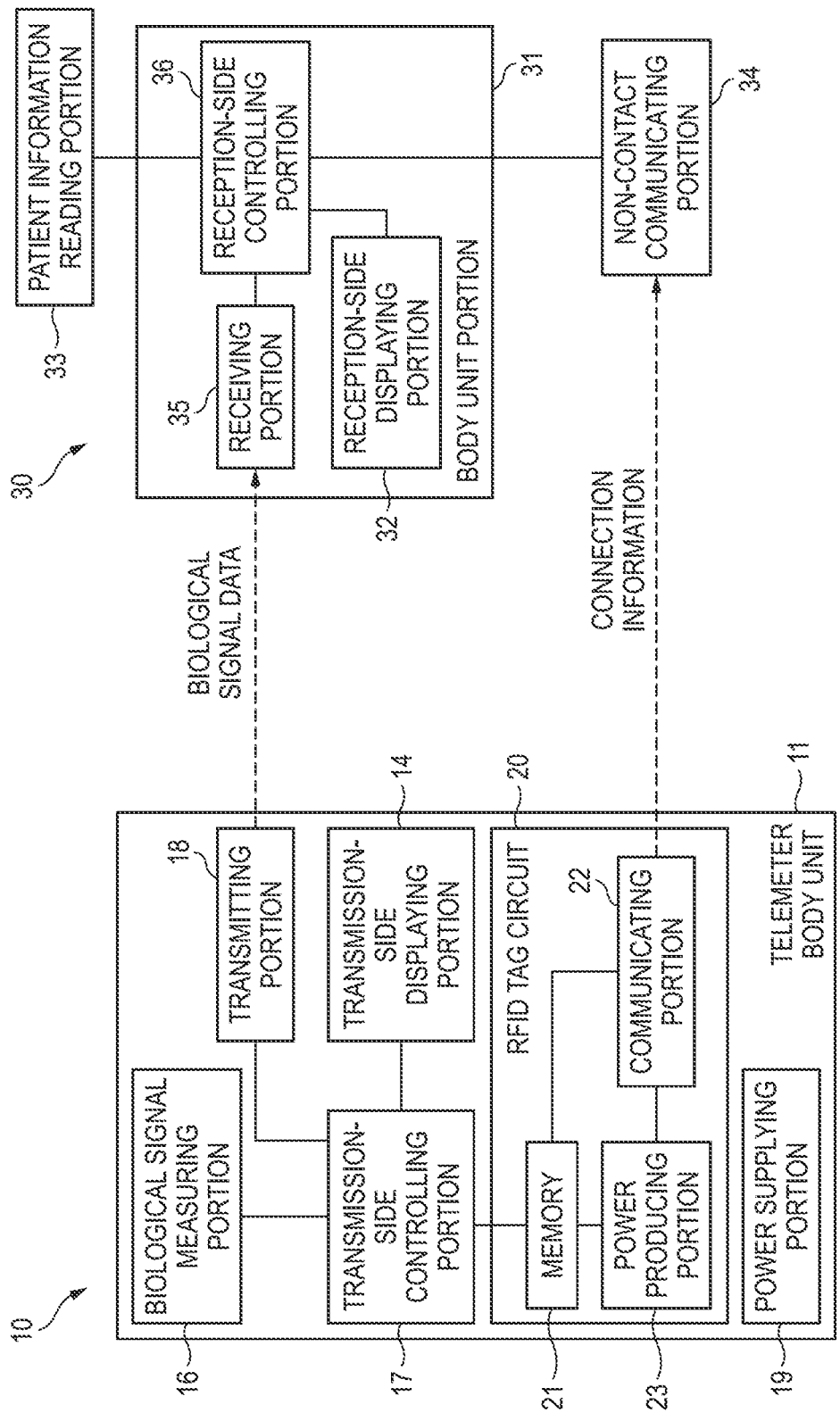
FIG. 3 is a block diagram showing the configurations of the medical telemeter and the receiver of FIG. 2.

FIG. 3 schematically shows in more detail the configurations of the telemeter 10 and the receiver 30.

The telemeter 10 includes a biological signal measuring portion 16, a transmission-side controlling portion 17, a transmitting portion 18, a power supplying portion 19, and the RFID tag circuit 20.

The biological signal measuring portion 16 is configured as an interface to which the electrode group 12 and sensor probe 13 that are described above are connected, and relays the various input biological signals to the transmission-side controlling portion 17.

The transmission-side controlling portion 17 includes calculating elements such as a CPU, and storage elements such as a memory, and is configured so as to be able to control the components of the telemeter 10. Moreover, the transmission-side controlling portion 17 is configured so as to be able to apply various processes such as A/D conversion on the various biological signals relayed from the biological signal measuring portion 16 to convert the signals to data in the format which can be stored in the memory, those in the format which is visible via the transmission-side displaying portion 14, and those in the format which is wirelessly communicated to the receiver 30 through the transmitting portion 18. The data stored in the memory of the transmission-side controlling portion 17 can be adequately referred to be displayed on the transmission-side displaying portion 14.

The transmitting portion 18 is an interface including an antenna, and configured so as to be able to wirelessly transmit the biological signal data produced by the transmission-side controlling portion 17, toward the receiver 30. A specific carrier frequency (wireless communication channel) is allocated to the telemeter 10, and the biological signal data are transmitted at the carrier frequency from the transmitting portion 18. The transmission-side controlling portion 17 and the transmitting portion 18 function as the communicating portion 83 in the invention.

The wireless communication channel is stored in the memory of the transmission-side controlling portion 17 as information (connection information) for establishing communication between the telemeter 10 and the receiver 30. The telemeter may be configured so that the allocated wireless communication channel can be changed by connecting the telemeter body unit 11 to a dedicated channel registering apparatus. In this case, the connection information stored in the memory of the transmission-side controlling portion 17 is rewritten. The memory of the transmission-side controlling portion 17 functions as the connection information storing portion 81 in the invention.

The power supplying portion 19 is a battery which can supply required electric power to the components constituting the telemeter 10. The power supplying portion 19 may be a disposable battery, or a rechargeable battery which is connected to a commercial power supply as required, and which is rechargeable. The power supplying portion 19 may be configured so that the portion is directly connected to a commercial power supply, the voltage of the commercial power supply is converted to voltages by which the components are driven, and the converted voltage is supplied.

The RFID tag circuit 20 is a part of an IC chip including a memory 21, and configured so as to transmit and receive data with the transmission-side controlling portion 17. In the embodiment, the circuit is configured so as to acquire at an adequate timing and store the connection information stored in the memory of the transmission-side controlling portion 17.

Therefore, at least one of the memory of the transmission-side controlling portion 17 and the memory 21 of the RFID tag circuit 20 functions as the connection information storing portion in the invention.

The body unit portion 31 of the receiver 30 includes the receiving portion 35 and a reception-side controlling portion 36.

The receiving portion 35 is an interface including an antenna, and configured so as to be able to receive the biological signal data which are wirelessly transmitted from the telemeter 10. The various received biological signal data are relayed to the reception-side controlling portion 36. The receiving portion 35 is configured so as to be able to tune to an arbitrary frequency in a predetermined band, and can receive biological signals simultaneously or selectively from a plurality of telemeters of different carrier frequencies.

The reception-side controlling portion 36 includes calculating elements such as a CPU, and storage elements such as a memory, and is configured so as to be able to control the components of the receiver 30. Moreover, the reception-side controlling portion is configured so as to be able to apply various processes on the various biological signals relayed from the receiving portion 35 to convert the signals to data in the format which can be stored in the memory, and those in the format which is visible via the reception-side displaying portion 32. Information stored in the memory of the reception-side controlling portion 36, such as the patient information acquired by the patient information reading portion 33 is adequately referred to be displayed on the reception-side displaying portion 32. Therefore, the memory of the reception-side controlling portion 36 functions as the first patient information storing portion 92 in the invention.

The non-contact communicating portion 34 is configured so as to be able to transfer data to the reception-side controlling portion 36. Information received by the non-contact communicating portion 34 is stored in the memory of the reception-side controlling portion 36, and adequately referred to be viewable on the reception-side displaying portion 32.

The RFID tag circuit 20 of the telemeter 10 includes a communicating portion 22 and a power producing portion 23 in addition to the memory 21.

The communicating portion 22 is an interface including an antenna, and configured so as to be able to transmit the connection information stored in the memory 21, toward the non-contact communicating portion 34.

The power producing portion 23 has a configuration in which, when the telemeter body unit 11 is caused to approach (hold over) the non-contact communicating portion 34, the portion generates electric power. Even in the case where electric power is not supplied from the power supplying portion 19 to the RFID tag circuit 20 in a state where a battery is not mounted on the telemeter body unit 11, the memory 21 can be subjected to a rewriting or reading operation by electric power which is received from the non-contact communicating portion 34. Moreover, driving of the communicating portion 22 is assisted, and transmission and reception of information to and from the non-contact communicating portion 34 are enabled. In a state where a battery is mounted on the telemeter body unit 11, data are exchanged between the memory 21 and the transmission-side controlling portion 17 by electric power supplied from the power supplying portion 19. The above-described operations, i.e., the rewriting or reading of the memory 21, the assistance of driving of the communicating portion 22, and transmission and reception of information to and from the non-contact communicating portion 34 can be performed by the electric power supplied from the non-contact communicating portion 34.

Based on the above description, referring again to FIG. 2, the operation of the medical telemetry system of the embodiment will be described. A case where a patient named ABC (hereinafter, referred to patient ABC) takes a procedure of entering a bed (hospital admission), and uses a bed of bed No. 1 while the telemeter 10 to which channel No. 1 is allocated is attached to the patient will be considered.

When the ID card 37 on which patient information identifying patient ABC is stored is issued, the patient information is read in the procedure of hospital admission by the patient information reading portion 33, and patient ABC is registered in the receiver 30. As described above, the patient information is stored in the memory of the reception-side controlling portion 36. Then, the telemeter body unit 11 to which channel No. 1 is allocated is caused to approach (hold over) the non-contact communicating portion 34, whereby non-contact communication (the first non-contact communication in the invention) is performed between the non-contact communicating portion 34 and the RFID tag circuit of the telemeter 10. Specifically, the connection information (channel No. 1) stored in the memory 21 of the RFID tag circuit 20 is transmitted to the non-contact communicating portion 34, and stored in the memory of the reception-side controlling portion 36 to be corresponded to the patient information. Therefore, the memory of the reception-side controlling portion 36 functions as the storage portion 91 in the invention.

The receiver 30 in the embodiment is configured so as to, after checking the storing of the connection information, start the reception of biological signal data through the receiving portion 35. According to the configuration, in the receiver 30, the patient information and the connection information are corresponded to each other simply by holding the telemeter body unit 11 over the non-contact communicating portion 34, and the communicable state is established. Matching (correspondence) of patient information and connection information is not required to be manually performed. Consequently, the configuration can contribute to laborsaving, and prevent a medical accident due to an erroneous input from occurring.

When the connection information is transmitted from the medical telemeter 10 to the receiver 30, the times which are internally managed in the both apparatuses respectively may be synchronized with each other. In the case where the both apparatuses include internal clocks respectively, for example, the transmission-side controlling portion 17 and the reception-side controlling portion 36 perform a process of matching their times with each other. In the case where the both apparatuses include timers respectively, the transmission-side controlling portion 17 and the reception-side controlling portion 36 perform a process of causing the timers to simultaneously start the time measurement. The configuration where the telemeter and the receiver can ensure simultaneousness of biological signal data as described above can avoid a situation where a temporal discrepancy is produced between the biological signal measured by the medical telemeter 10 and that received by the receiver 30.

In the embodiment, the reading apparatus in which the RFID tag circuit 20 performs a part of the function of the connection information storing portion 81 and non-contact communication between the non-contact communicating portion 34 and the RFID tag circuit 20 is enabled has been exemplarily described. However, the following configurations may be employed.

A configuration may be employed in which a mark in which a bar code, or QR code or Aztec code (both are registered trademarks) in which the above-described connection information is stored is attached to the telemeter body unit 11, and the mark is read by a code reader functioning as the non-contact communicating portion 34, so that the receiver 30 acquires the connection information. Namely, the code functions as the connection information storing portion 81. In the case where the patient information reading portion 33 is configured by a similar code reader, the code reader can be shared by the portion and the non-contact communicating portion 34, thereby contributing to reduced size and cost of the apparatus.

The connection information is requested to contain at least one of the allocated channel number of the wireless communication, the product number of the telemeter 10, the allocated bed number, and the like. In the case where the telemeter 10 can function in a similar manner as a portable information terminal which operates on a wireless network, i.e., the case where biological signal data are transmitted through a wireless network, an IP address and a MAC address may be contained as connection information.

A configuration may be employed in which the above-described bar code or two-dimensional code is converted to data to be stored in the memory of the transmission-side controlling portion 17, and then displayed in response to a predetermined operation on the transmission-side displaying portion 14 to be read by a code reader. Unlike the configuration where a mark is attached to the telemeter body unit 11, the contents of connection information can be changed as required.

A configuration may be employed in which the non-contact communicating portion 34 is formed by a transmitter of infrared communication, and the telemeter 10 incorporates a transmitter of infrared communication. In this case, the connection information stored in the memory of the transmission-side controlling portion 17 is adequately converted to a data format which can be used in infrared communication, and then transmitted from the telemeter 10 to the receiver 30.

Figure 4:
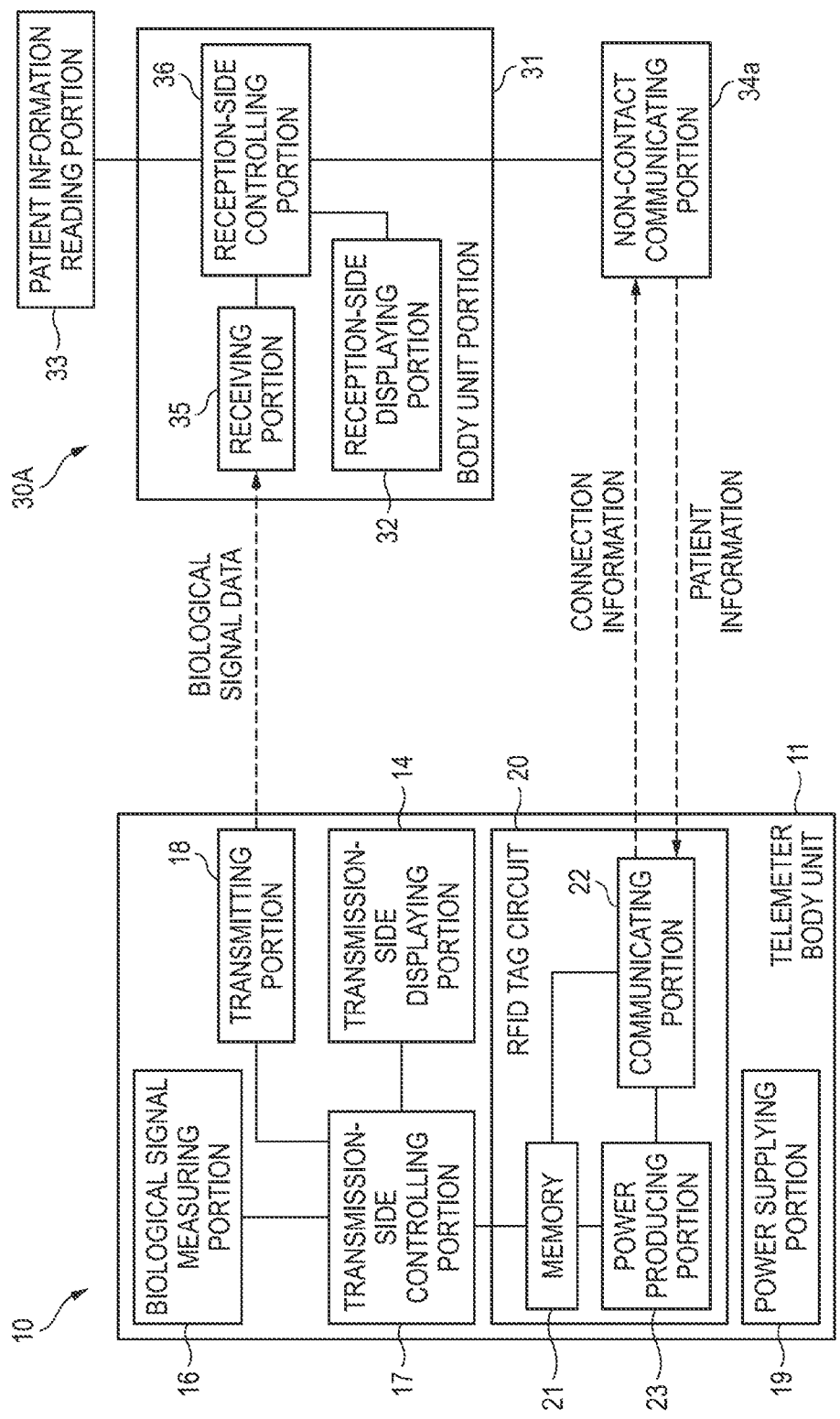
FIG. 4 is a block diagram showing the configurations of a medical telemeter and receiver which constitute a medical telemetry system of a second embodiment of the invention.

Next, a medical telemetry system 200 of a second embodiment of the invention will be described with reference to FIG. 4. The components which are identical or similar to those of the first embodiment are denoted by the same reference numerals, and duplicated description will be omitted.

In the embodiment, an RFID reader/writer is used as a non-contact communicating portion 34a of a receiver 30A. In addition to the reading function which has been described in the first embodiment, and in which the information stored in the memory 21 of the RFID tag circuit 20 is read, namely, the embodiment has a function of writing information in the memory.

Specifically, the non-contact communicating portion 34a is configured so as to be able to transmit and receive data to and from the reception-side controlling portion 36. Information received by the non-contact communicating portion 34a is stored in the memory of the reception-side controlling portion 36, and adequately referred to be viewable on the reception-side displaying portion 32. Patient information stored in the memory of the reception-side controlling portion 36 can be transmitted to the RFID tag circuit 20 of the telemeter 10 through the non-contact communicating portion 34a. In the embodiment, the name of a patient is set as the patient information.

The memory 21 of the RFID tag circuit 20 is configured so as to be able to transmit and receive data to and from the transmission-side controlling portion 17, and the patient information which is received from the non-contact communicating portion 34a, and which is stored in the memory 21 is stored at an adequate timing in the memory of the transmission-side controlling portion 17. Therefore, at least one of the memory of the transmission-side controlling portion 17 and the memory 21 of the RFID tag circuit 20 functions as the second patient information storing portion 82 in the invention.

Based on the above description, the operation of the medical telemetry system 200 of the embodiment will be described. In the same manner as the first embodiment, a case where patient ABC takes a procedure of entering a bed (hospital admission), and uses a bed of bed No. 1 while the telemeter 10 to which channel No. 1 is allocated is attached to the patient will be considered.

When the ID card 37 on which the patient information identifying patient ABC is stored is issued, the patient information is read in the procedure of hospital admission by the patient information reading portion 33, and patient ABC is registered in the receiver 30A. As described above, the patient information is stored in the memory of the reception-side controlling portion 36. Then, the telemeter body unit 11 to which channel No. 1 is allocated is caused to approach (hold over) the non-contact communicating portion 34a, whereby non-contact communication is performed between the non-contact communicating portion 34a and the RFID tag circuit 20 of the telemeter 10. Specifically, the patient information stored in the memory of the reception-side controlling portion 36 is transmitted from the non-contact communicating portion 34a, and stored in the memory 21 of the RFID tag circuit 20 (the second non-contact communication in the invention). In the embodiment, the patient's name ABC is set as the patient information. By contrast, the connection information (channel No. 1) stored in the memory 21 of the RFID tag circuit 20 is transmitted to the non-contact communicating portion 34a, and stored in the memory of the reception-side controlling portion 36 (the first non-contact communication in the invention).

The telemeter 10 in the embodiment is configured so as to, after checking the storing of the patient information, start the transmission of biological signal data through the transmitting portion 18. By contrast, the receiver 30A is configured so as to, after checking the storing of the connection information, start the reception of biological signal data through the receiving portion 35. According to the configuration, the patient information and the connection information are stored in both the telemeter 10 and the receiver 30A simply by holding the telemeter body unit 11 over the non-contact communicating portion 34a, and the communicable state is established. Matching (correspondence) of patient information and connection information is not required to be manually performed. Consequently, the configuration can contribute to laborsaving, and prevent a medical accident due to an erroneous input from occurring.

Figure 5:
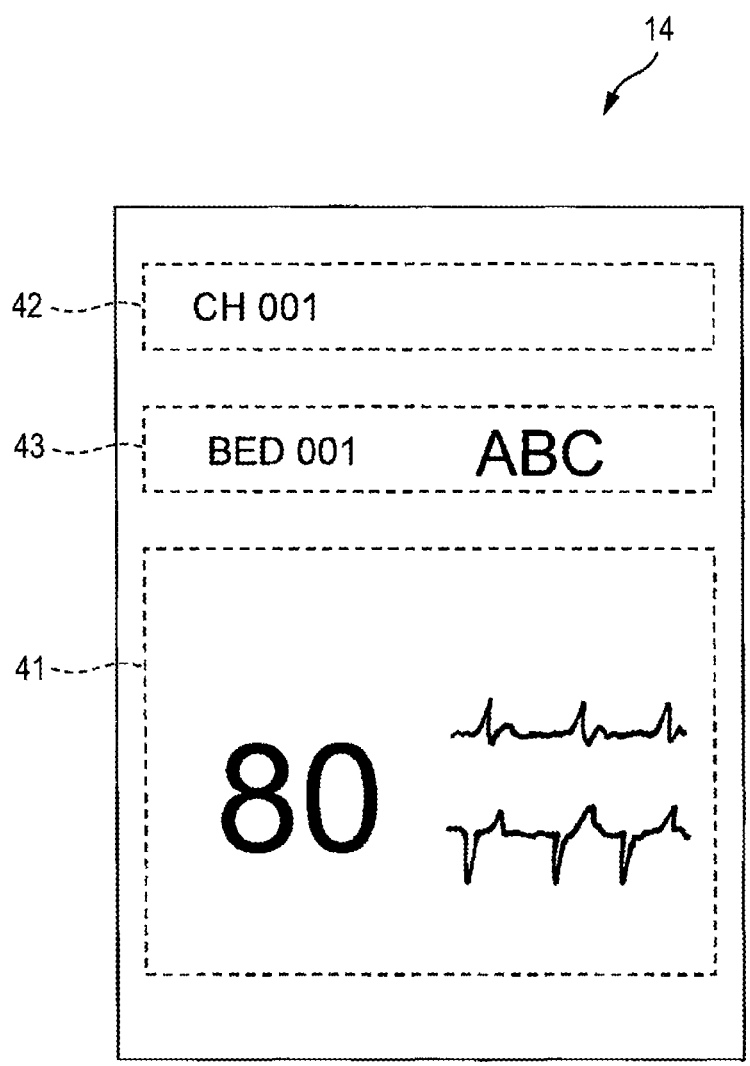
FIG. 5 is a view schematically showing an example of a transmission-side displaying portion which is disposed in the medical telemeter of FIG. 4.

As shown in FIG. 5, in the transmission-side displaying portion 14 disposed in the telemeter body unit 11 in the embodiment, a patient information display area 43 where patient information acquired from the receiver 30A is displayed is disposed in addition to a biological signal display area 41 where biological signal data acquired through the electrode group 12 and the sensor probe 13 are displayed, and a connection information display area 42 where the channel number is displayed. In the embodiment, the patient's name ABC is displayed in the patient information display area 43. Since the name of a patient is displayed on the transmission-side displaying portion 14 disposed in the telemeter body unit 11 which is to be directly attached to the patient, an accident in which the telemeter 10 is erroneously attached to another patient can be prevented from occurring.

In the patient information, the bed number may be displayed in addition to or in place of the patient's name, and image information such as a face photograph of the patient may be displayed in addition to or in place of character information such as the patient's name. Since the space for the transmission-side displaying portion 14 is limited, the connection information display area 42 may be omitted.

On the other hand, the data stored in the memory of the reception-side controlling portion 36 can be displayed on the reception-side displaying portion 32, and hence patient information and connection information, i.e., the patient's name and the channel number which is used by the telemeter 10 are displayed on the reception-side displaying portion 32. The biological signal data transmitted from this telemeter 10 are displayed together with these sets of information, and therefore biological signals of a desired patient can be displayed and monitored together with correct patient information. Moreover, matching (correspondence) of patient information and connection information which can establish this state can be completed without performing a manual inputting work which is cumbersome, and which may possibly cause an error.

When the patient is to leave the bed (leave the hospital), a mode of the procedure of leaving a bed is activated in the receiver 30A, and then the telemeter 10 is held over the non-contact communicating portion 34a. This process is called the bed leaving process.

In the receiver 30A, the patient information and connection information stored in the memory of the reception-side controlling portion 36 are deleted, and a patient information deletion command is transmitted to the RFID tag circuit 20 of the telemeter 10 through the non-contact communicating portion 34a. When the RFID tag circuit 20 receives the patient information deletion command, the transmission-side controlling portion 17 deletes the patient information which is stored in the memory 21 of the RFID tag circuit 20 and the memory of the transmission-side controlling portion 17. As a result, communication between the telemeter 10 and the receiver 30A is disabled.

When connection information is transmitted from the medical telemeter 10 to the receiver 30A, or when patient information is transmitted from the receiver 30A to the medical telemeter 10, the times which are internally managed in the both apparatuses respectively are synchronized with each other. In the case where the both apparatuses include internal clocks respectively, for example, the transmission-side controlling portion 17 and the reception-side controlling portion 36 perform a process of matching their times with each other. In the case where the both apparatuses include timers respectively, the transmission-side controlling portion 17 and the reception-side controlling portion 36 perform a process of causing the timers to simultaneously start the time measurement. The configuration where the telemeter and the receiver can ensure simultaneousness of biological signal data as described above can avoid a situation where a temporal discrepancy is produced between the biological signal measured by the medical telemeter 10 and that received by the receiver 30A.

The connection information storing portion 81 and the non-contact communicating portion 34a can be variously modified as described in the first embodiment. In the case where the non-contact communication is performed by infrared communication, an infrared communication device having the transmitting/receiving function is disposed in both the non-contact communicating portion 34a and the telemeter 10. In the embodiment, the example in which the first non-contact communication and the second non-contact communication are performed by the same kind of communication system (RFID) has been described. Alternatively, the communications may be performed by different communication systems. In the case where the connection information storing portion 81 is realized by code information, for example, the non-contact communicating portion 34a is configured by a code reader and an RFID writer. The RFID writer may be replaced with a transmitter which uses a beacon or the like, and which corresponds to the specified low power radio communication (antenna power: 250 μW). In this case, the medical telemeter 10 includes a receiver corresponding to the specified low power radio communication.

Figure 6:
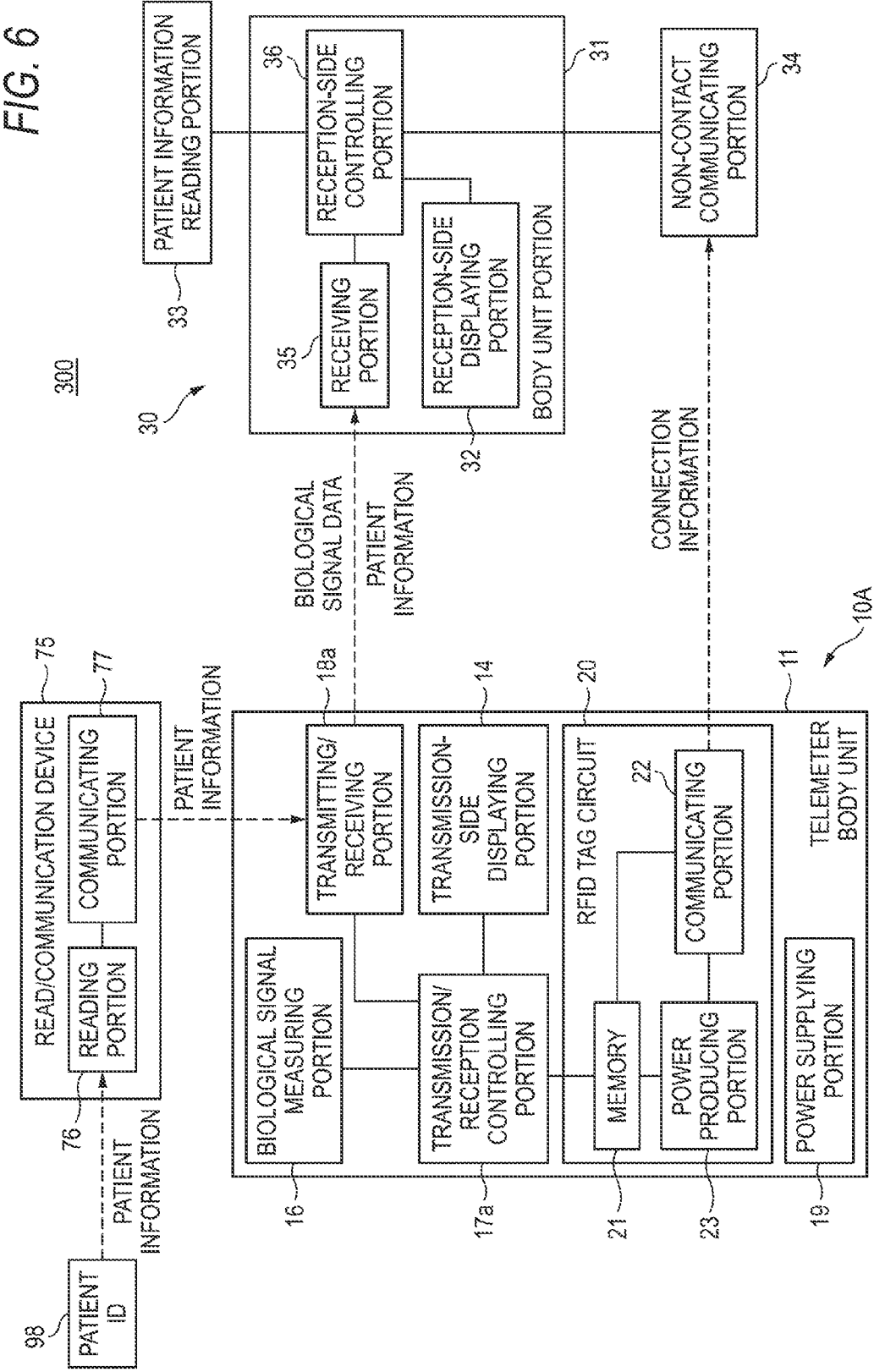
FIG. 6 is a block diagram showing the configurations of a medical telemeter and receiver which constitute a medical telemetry system of a third embodiment of the invention.

Next, a medical telemetry system 300 of a third embodiment of the invention will be described with reference to FIG. 6. The components which are identical or similar to those of the first embodiment are denoted by the same reference numerals, and duplicated description will be omitted.

The medical telemetry system 300 of the embodiment is configured by a medical telemeter 10A, the receiver 30, and the read/communication device 75. The medical telemeter 10A includes a transmission/reception controlling portion 17a and a transmitting/receiving portion 18a. The read/communication device 75 includes a reading portion 76 and a communicating portion 77. These portions function as the communicating portion in the invention.

A patient ID 98 (the third patient information storing portion in the invention) is to be attached to a patient, and carries information identifying the patient. For example, a mark in which a two-dimensional code which can identify a patient, such as a bar code, or QR code or Aztec code (both are registered trademarks), or a face photograph of the patient is recorded is attached to a band, and the band is attached to the wrist or the like of the patient. Alternatively, an RFID tag including a memory which stores information identifying the patient may be attached to the patient.

The reading portion 76 of the read/communication device 75 is configured so as to be able to read the patient information carried by the patient ID 98. In the case where the patient information is code information such as a bar code, the reading portion 76 is configured as a code reader, and, in the case where the patient information is image information such as a face photograph, the reading portion is configured as an image recognition device. In the case where the patient information is information stored in a memory of the RFID tag, the reading portion is configured as an RFID reader.

The communicating portion 77 of the read/communication device 75 is configured so as to be able to transmit the patient information read by the reading portion 76 to the transmitting/receiving portion 18a of the medical telemeter 10A. By contrast, the transmitting/receiving portion 18a is configured so as to be able to, under control of the transmission/reception controlling portion 17a, transmit the patient information received from the communicating portion 77 to the receiver 30.

The reception-side controlling portion 36 of the receiver 30 is configured so as to be able to determine whether the patient information received by the receiving portion 35 is coincident with that stored in the memory of the reception-side controlling portion 36 or not, and, if not coincident, issue an alarm.

According to the medical telemetry system 300 of the embodiment, in addition to the operations and functions which have been described in the first embodiment, the correspondence relationship between a patient and the medical telemeter 10A can be rechecked when the medical telemeter 10A is to be attached to the patient.

When the medical telemeter 10A is to be attached to a patient, a medical person such as a nurse reads the patient information carried by the patient ID 98, by using the read/communication device 75. In this state, the patient information is transmitted from the read/communication device 75 to the medical telemeter 10A. Furthermore, the patient information is transmitted from the transmitting/receiving portion 18a of the medical telemeter 10A to the receiver 30, and the receiver 30 determines coincidence of the patient information. If the patient information is not coincident, i.e., if the medical telemeter 10A is not attached to the patient to which the medical telemeter 10A is to be originally attached, an alarm is issued, and the medical person can recognize the error. Therefore, it is possible to more surely prevent a medical accident due to misidentification of patients, from occurring.

Alternatively, a configuration may be employed in which the alarm generating function is omitted, the patient information received from the medical telemeter 10A is displayed on the reception-side displaying portion 32 of the receiver 30, and coincidence of the patient information is visually checked.

In the embodiment, the correspondence relationship between a patient and the medical telemeter is checked by using the read/communication device 75. Therefore, the connection information display area 42 and patient information display area 43 of the transmission-side displaying portion 14 of the medical telemeter 10A can be omitted, and this contributes to cost reduction of a medical telemeter.

The communication between the communicating portion 77 of the read/communication device 75 and the transmitting/receiving portion 18a of the medical telemeter 10A is performed by means of wireless or wired communication. Examples of wireless communication are the infrared communication, the specified low power radio communication (antenna power: 250 µW), Bluetooth (registered trademark), and REID tag communication. An example of wired communication is wired connection based on standards such as USE or RS-232C.

The read/communication device 75 may be configured as a device which is independent from the medical telemeter 10A, or a part of the medical telemeter 10A.

Figure 7:
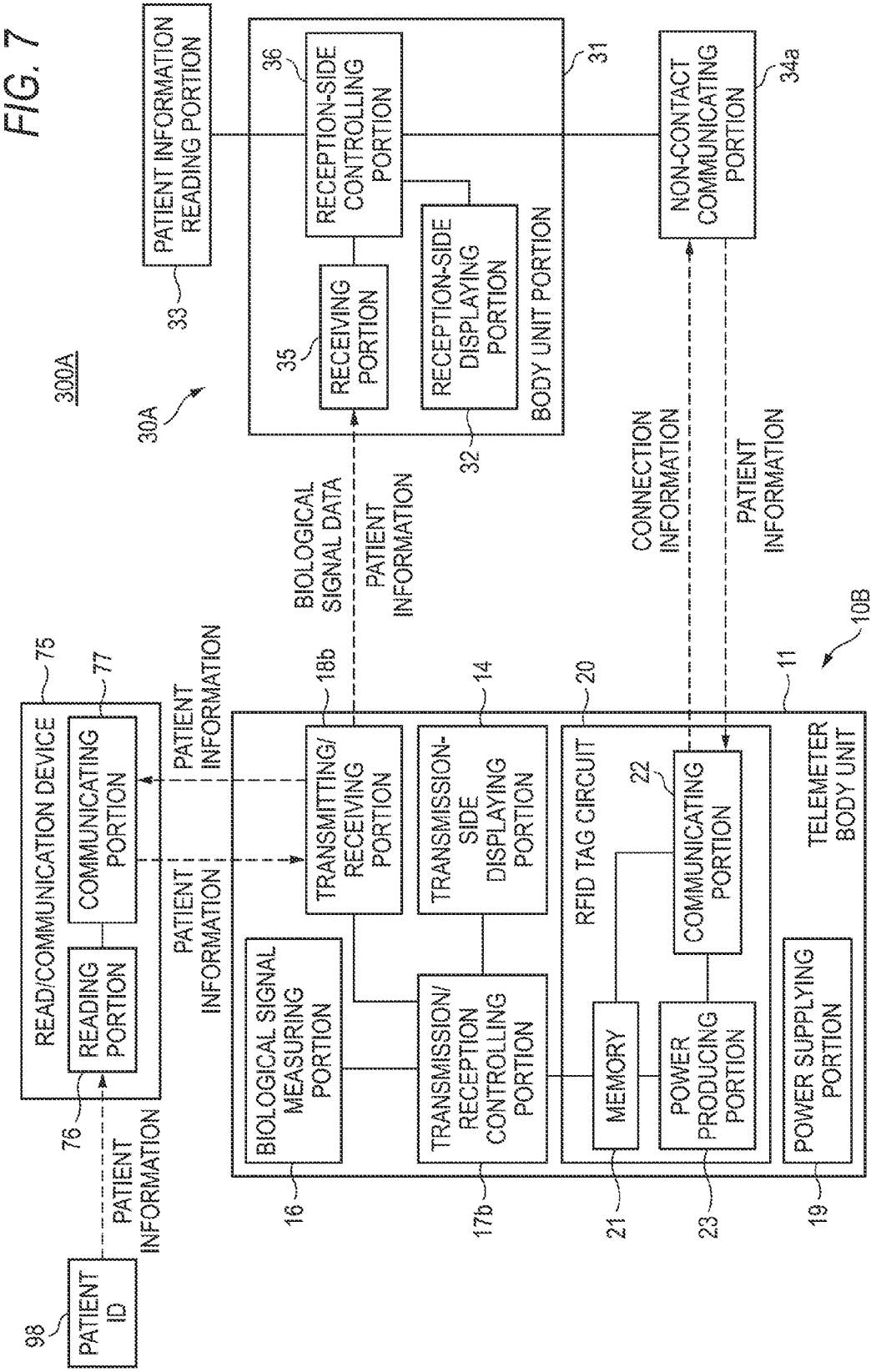
FIG. 7 is a block diagram showing the configurations of a medical telemeter and receiver which constitute a medical telemetry system of a fourth embodiment of the invention.

Next, a medical telemetry system 300A of a fourth embodiment of the invention will be described with reference to FIG. 7. The components which are identical or similar to those of the second and third embodiments are denoted by the same reference numerals, and duplicated description will be omitted.

The medical telemetry system 300A of the embodiment is configured by a medical telemeter 10B, the receiver 30A, and the read/communication device 75. The medical telemeter 10B includes a transmission/reception controlling portion 17b and a transmitting/receiving portion 18b. These portions function as the communicating portion in the invention.

The communicating portion 77 of the read/communication device 75 is configured so as to be able to transmit the patient information read by the reading portion 76 to the transmitting/receiving portion 18b of the medical telemeter 10B. By contrast, the transmitting/receiving portion 18b is configured so as to be able to, under control of the transmission/reception controlling portion 17b, transmit the patient information received from the communicating portion 77 to the receiver 30A. The transmitting/receiving portion 18b is configured so as to be able to, under control of the transmission/reception controlling portion 17b, transmit the patient information stored in the memory 21 of the RFID tag circuit 20 to the communicating portion 77 of the read/communication device 75.

The read/communication device 75 is configured so as to determine whether the patient information read by the reading portion 76 is coincident with that received by the communicating portion 77 from the transmitting/receiving portion 18b of the medical telemeter 10B or not, and, if not coincident, issue an alarm. The transmission/reception controlling portion 17b of the medical telemeter 10B is configured so as to determine whether the patient information stored in the memory 21 is coincident with that received by the transmitting/receiving portion 18b from the communicating portion 77 of the read/communication device 75 or not, and, if not coincident, issue an alarm.

According to the medical telemetry system 300A of the embodiment, in addition to the operations and functions which have been described in the second embodiment, the correspondence relationship between a patient and the medical telemeter 10B can be rechecked when the medical telemeter 10B is to be attached to the patient.

When the medical telemeter 10B is to be attached to a patient, a medical person such as a nurse reads the patient information carried by the patient ID 98, by using the read/communication device 75. In this state, at least one of transmission from the read/communication device 75 to the medical telemeter 10B, and that from the medical telemeter 10B to the read/communication device 75 is executed. As described above, at least one of the read/communication device 75 and the medical telemeter 10B determines coincidence of the patient information. If the patient information is not coincident, i.e., if the medical telemeter 10B is not attached to the patient to which the medical telemeter 10B is to be originally attached, an alarm is issued, and the medical person can recognize the error. Therefore, it is possible to more surely prevent a medical accident due to misidentification of patients, from occurring.

Alternatively, a configuration may be employed in which the alarm generating function of the read/communication device 75 is omitted, the patient information received from the medical telemeter 10B is displayed on a displaying portion (not shown) of the read/communication device 75, and coincidence of the patient information is visually checked. Moreover, a configuration may be employed in which the alarm generating function of the medical telemeter 10B is omitted, the patient information received from the read/communication device 75 is displayed on the transmission-side displaying portion 14 of the medical telemeter 10B, and coincidence of the patient information is visually checked.

A configuration may be employed in which, in the case where patient information is to be transmitted from the transmitting/receiving portion 18b of the medical telemeter 10B to the receiver 30A, the reception-side controlling portion 36 of the receiver 30A determines whether the patient information received by the receiving portion 35 is coincident with that stored in the memory of the reception-side controlling portion 36 or not, and, if not coincident, issues an alarm. Also in this case, it is possible to more surely prevent a medical accident due to misidentification of patients, from occurring.

Alternatively, a configuration may be employed in which the alarm generating function of the receiver 30A is omitted, the patient information received from the medical telemeter 10B is displayed on the reception-side displaying portion 32 of the receiver 30A, and coincidence of the patient information visually checked.

In a hospital, usually, a plurality of telemeters are used in order to monitor the conditions of a plurality of inpatients. A bedside monitor is disposed in the vicinity of a bed for each patient, and communicably connected to a central monitor disposed in a nurse's station or the like. A case where the invention is applied to a medical telemetry system which, as described above, includes a plurality of telemeters, a plurality of bedside monitors, and a central monitor will be described with reference to FIG. 8. It is a matter of course that all the above-described embodiments can be applied to such a system.

Figure 9:
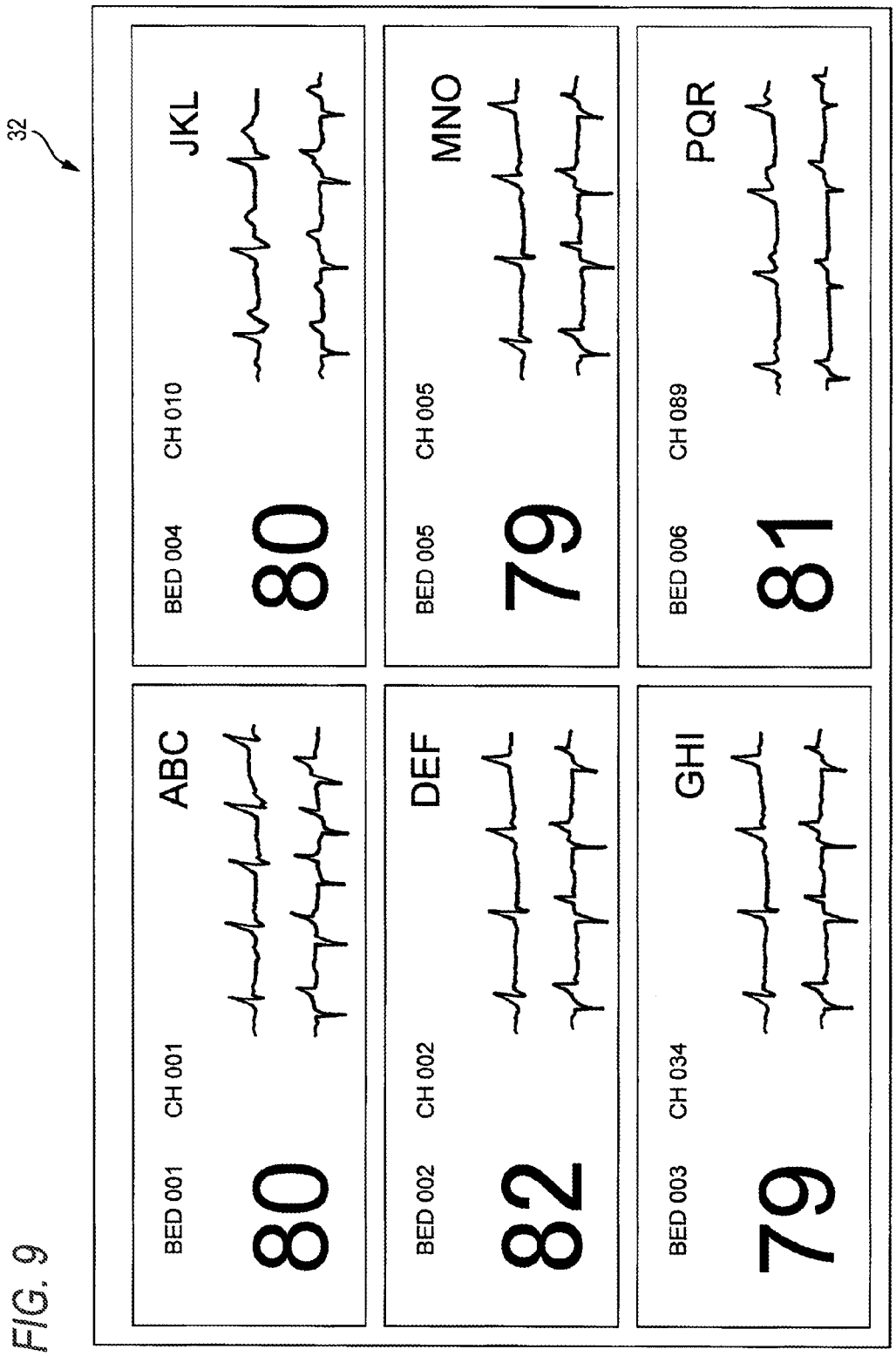
FIG. 9 is a view schematically showing an example of a displaying portion of a central monitor in the medical telemetry system of FIG. 8.

An n number of bedside monitors 60a, 60b, . . . , 60n are connected in a mutually communicable manner to a central monitor 50 through a LAN. When a patient is in the bed, the biological signals of the patient are directly supplied to the corresponding bedside monitor, and relayed to the central monitor 50. In the central monitor 50, a displaying portion on which a monitor screen such as shown in FIG. 9 is displayed is disposed, so that the conditions of patients can be centrally managed.

In the following description, in the case where one of the plurality of bedside monitors 60a, 60b, . . . , 60n is not particularly specified, the bedside monitor is referred to as "bedside monitor 60" for the sake of convenience.

When a patient leaves the bed, biological signal data of the patient are wirelessly transmitted through the telemeter attached to the patient, and monitored by the central monitor 50. A configuration may be employed in which a signal transmitted from the telemeter is directly received by the central monitor 50, or in which the signal is once received by the bedside monitor 60, and then relayed to the central monitor 50.

Specific transmission carrier frequencies (i.e., channels) are allocated to a plurality of telemeters 10a, 10b, . . . , 10n, respectively. In the embodiment, the frequencies are selected from a band ranging from 420 to 450 MHz. In the following description, in the case where one of the plurality of telemeters 10a, 10b, . . . , 10n is not particularly specified, the bedside monitor is referred to as "telemeter 10" for the sake of convenience.

Figure 8:
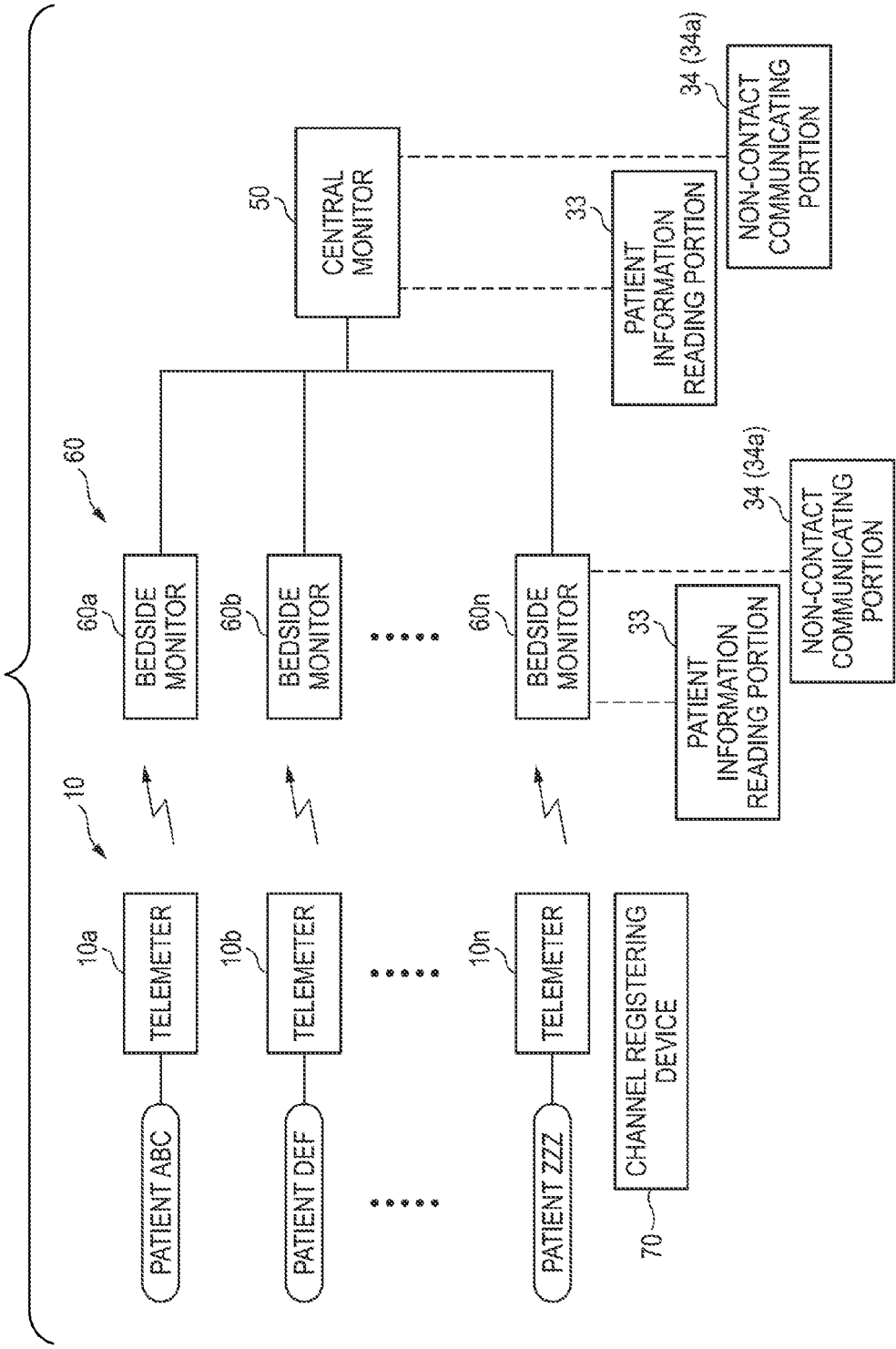
FIG. 8 is a view schematically showing a case where the medical telemetry system of the invention includes a plurality of medical telemeters.

In the example of FIGS. 8 and 9, patient ABC is in the bed of No. 1 in which the bedside monitor 60a is disposed, and the telemeter 10a to which channel 1 is allocated is attached to the patient. Similarly, patient DEF is in the bed of No. 2 in which the bedside monitor 60b is disposed, and the telemeter 10b to which channel 2 is allocated is attached to the patient, and patient ZZZ is in the bed of No. n in which the bedside monitor 60n is disposed, and the telemeter 10n to which channel n is allocated is attached to the patient. Each of the telemeters 10 in the embodiment is configured so that the telemeter is connected to a dedicated channel registering device 70 and the initial value of the channel can be changed. Alternatively, a configuration in which the initial value cannot be changed may be employed.

In the case where the central monitor 50 is to function as the above-described receiver 30, the patient information reading portion 33 and the non-contact communicating portion 34 (or 34a) are communicably connected to the central monitor 50. When each of the plurality of telemeters 10 is held over the non-contact communicating portion 34 (or 34a), the above-described process of automatically matching patient information with connection information is executed. The above-described reception-side controlling portion 36 is disposed in the central monitor 50, and the patient information which is acquired through the patient information reading portion 33 and the connection information which is acquired through the non-contact communicating portion 34a are stored in the memory of the reception-side controlling portion 36.

In addition to or in place of the configuration, a configuration may be employed in which at least one of the plurality of bedside monitors is caused to function as the receiver 30. In this case, the patient information reading portion 33 and the non-contact communicating portion 34 (or 34a) are communicably connected to the at least one bedside monitor (in FIG. 8, the bedside monitor 60n). Although the reception-side controlling portion 36 is disposed in the bedside monitor 60n, the acquired patient information and connection information must be transmitted to the central monitor 50 to be stored in a memory disposed in the central monitor 50. A configuration may be employed in which copies of the patient information and the connection information are held in the bedside monitor 60n.

Since the above-described process of automatically matching patient information with connection information is performed, laborsaving in the inputting work, and prevention of occurrence of a medical accident due to an erroneous input are enabled even in a telemeter system which includes a plurality of telemeters 10 as in the example. In a system which uses a plurality of telemeters, however, the following error may occur.

In the case where, after patient ABC is registered in the telemeter 10a, there arises a need to attach the telemeter 10b to patient ABC for any reason, when a process of registering patient ABC in the telemeter 10b is performed without conducting the above-described bed leaving process with respect to the telemeter 10a, one set of patient information is corresponded to two sets of connection information.

When, after patient ABC is registered in the telemeter 10a, a process of registering patient DEF in the telemeter 10a is erroneously performed without conducting the bed leaving process, plural sets of patient information are corresponded to one set of connection information.

Under these situations, a difference is produced between the patient which is recognized on the side of the receiver 30, and that from which biological signal data are actually transmitted, and hence there is a possibility that a serious medical accident may occur. In the embodiment, therefore, a configuration is employed where, when the receiver 30 detects a state where patient information and connection information are not correspondent to each other in one-to-one relationship, an alarm is issued. Here, the terms "patient information and connection information are not correspondent to each other in one-to-one relationship" are defined as "patient information of a certain patient is correspondent to plural sets of connection information" and "a state where certain specific connection information is correspondent to patient information of a plurality of patients".

Specifically, when the bed entering process, i.e., a process of registering a certain patient in a certain telemeter 10 is to be performed, the receiver 30 refers information stored in the memory of the reception-side controlling portion 36, and checks whether the one-to-one relationship is established or not. If a state where the above-described one-to-one relationship is not established for any reason is detected, the bed entering process is not completed, and an alarm is issued. Examples of the alarm are a display of a confirmation message on the reception-side displaying portion 32, production of a warning tone, and lighting of a warning lamp. A configuration may be employed in which, in addition to or in place of the bed entering process, the memory of the reception-side controlling portion 36 is periodically scanned, and it is checked whether the one-to-one relationship is established or not.

The transmitting portion 18 of each telemeter 10 may be configured so as to be able to transmit the stored patient information in addition to biological signal data. In this case, a configuration may be employed in which the receiver 30 compares the patient information received by the receiving portion 35 with the patient information which is stored in the memory of the reception-side controlling portion 36 in correspondence to the connection information that is used in the establishment of the communication with the telemeter 10, and, if the both are different from each other, an alarm is issued.

In the embodiment, the configuration where at least one of the central monitor 50 and the bedside monitor 60 is caused to function as the receiver 30 in the invention has been described. The invention is not limited to a communication system of transmitting biological signals between medical apparatuses, and may be applied to a system in which a biological signal measured by a medical apparatus can be transmitted to portable information terminals carried by medical persons. Specifically, a configuration may be employed in which the central monitor 50 and the bedside monitor 60 are set as telemeters and portable information terminals are caused to function as the receiver 30 in the invention. The portable information terminals may be those which operate only on a wireless LAN, or those which can be further connected to an external WAN.

In a cast that the central monitor 50 and the bedside monitor 60 are situated in predetermined places such as a nurse's station and a bed side, a medical person cannot check biological signals unless the person moves to one of the places. According to the configuration, by contrast, each medical person can always remotely check biological signals of a patient of which the medical person is in charge, and therefore the working efficiency can be improved.

The biological signal data which are received and displayed by a portable information terminal may be those which are directly transmitted from the telemeter 10, or those which are relayed through the bedside monitor 60 or the central monitor 50. Similarly, the connection information identifying the telemeter 10 may be directly acquired from the telemeter 10, or from the bedside monitor 60 or the central monitor 50. Connection information can be acquired through the above-described non-contact communication by using an RFID reader which is incorporated in a portable information terminal, or a code reader such as a camera, or employing an infrared communication function.

Although the medical telemetry system of the invention has been described based on the embodiments, the embodiments have been described in order to facilitate understanding of the invention, and are not intended to limit the invention. It is a matter of course that the invention may be changed or improved without departing the spirit thereof, and includes equivalent embodiments.

What is claimed is:

1. A medical telemetry system comprising:
    a medical telemeter including:
        a measuring portion which measures a biological signal of a patient as biological signal data;
        a communicating portion which wirelessly transmits the biological signal data; and
        a connection information storing portion which stores connection information; and
    a receiver including:
        a non-contact communicating portion which executes first non-contact communication to read the connection information in a non-contact manner;
        a storage portion which stores the connection information read by the non-contact communicating portion; and
        a receiving portion which starts reception of the biological signal data transmitted by the communicating portion, when the connection information is stored in the storage portion.

2. The medical telemetry system according to claim 1, wherein
    the receiver further includes a first patient information storing portion which stores patient information for identifying the patient,
    the medical telemeter further includes a second patient information storing portion, and
    the non-contact communicating portion of the receiver executes second non-contact communication to write the patient information that is stored in the first patient information storing portion in the second patient information storing portion in a non-contact manner, when the non-contact communicating portion executes the first non-contact communication.

3. The medical telemetry system according to claim 2, wherein the medical telemeter further includes a transmission-side displaying portion which displays the patient information stored in the second patient information storing portion.

4. The medical telemetry system according to claim 3, wherein the patient information includes at least one of character information and image information.

5. The medical telemetry system according to claim 2, wherein the receiver further includes a reception-side displaying portion which displays at least one of the biological signal data and the patient information and the connection information in a manner that the patient information and the connection information correspond to each other.

6. The medical telemetry system according to claim 2, wherein the receiver issues an alarm when a state where the patient information is not corresponded to the connection information in one-to-one relationship is detected.

7. The medical telemetry system according to claim 2, wherein
    the communicating portion of the medical telemeter transmits patient information which is stored in the second patient information storing portion to the receiving portion of the receiver together with the biological signal data, and
    the receiver compares the patient information that is received by the receiving portion with the patient information that is stored in the first patient information storing portion of the receiver, and
    the receiver issues an alarm, when a state where the patient information that is received by the receiving portion and the patient information that is stored in the first patient information storing portion are different from each other is detected.

8. The medical telemetry system according to claim wherein the connection information storing portion includes one of an RFID chip, a bar code, and a two-dimensional code.

9. The medical telemetry system according to claim 2, wherein the second patient information storing portion includes an RFID chip.

10. The medical telemetry system according to claim 1, wherein the connection information includes one of a wireless communication channel, a device identification number, an IP address, and a MAC address.

11. The medical telemetry system according to claim wherein
    the medical telemeter includes a transmitter which is portable by the patient, and
    the receiver includes at least one of a bedside monitor and a central monitor.

12. The medical telemetry system according to claim wherein
    the medical telemeter includes at least one of a transmitter which is portable by the patient, a bedside monitor, and a central monitor, and
    the receiver includes a portable information terminal.

13. The medical telemetry system according to claim 1, wherein, when the non-contact communicating portion of the receiver executes the first non-contact communication, times which are internally managed in the medical telemeter and the receiver respectively are synchronized with each other.

14. The medical telemetry system according to claim 2, wherein, when the non-contact communicating portion of the receiver executes one of the first non-contact communication and the second non-contact communication, times which are internally managed in the medical telemeter and the receiver respectively are synchronized with each other.

15. The medical telemetry system according to claim 1 further comprising a read/communication device which, from a patient information storing portion, which is to be attached to a patient and which stores patient information identifying the patient, reads the patient information, and which transmits the read patient information to the communicating portion of the medical telemeter.

16. The medical telemetry system according to claim 2 further comprising a read/communication device which, from a third patient information storing portion, which is to be attached to a patient and which stores patient information for identifying the patient, reads the patient information, the read/communication device which executes at least one of transmission of the patient information read from the third patient information storing portion to the communicating portion of the medical telemeter, and reception of the patient information stored in the second patient information storing portion of the medical telemeter from the communicating portion of the medical telemeter.

17. The medical telemetry system according to claim 15, wherein the communicating portion of the medical telemeter transmits the patient information received from the read/communication device, to the receiver.

18. The medical telemetry system according to claim 16, wherein
the read/communication device executes the reception of the patient information from the communicating portion of the medical telemeter, and
the read/communication device issues an alarm when the patient information read from the third patient information storing portion is not coincident with the patient information received from the communicating portion of the medical telemeter.

19. The medical telemetry system according to claim 16, wherein
the read/communication device executes the transmission of the patient information to the communicating portion of the medical telemeter, and
the medical telemeter issues an alarm when the patient information received from the read/communication device is not coincident with the patient information stored in the second patient information storing portion.

20. The medical telemetry system according to claim 17, wherein the receiver issues an alarm when the patient information received from the communicating portion of the medical telemeter is not coincident with the patient information stored in the second patient information storing portion.

21. A medical telemeter which is to be used in the medical telemetry system according to claim 1.

* * * * *